US007063977B2

(12) United States Patent
Patel

(10) Patent No.: US 7,063,977 B2
(45) Date of Patent: Jun. 20, 2006

(54) ENZYMATIC RESOLUTION OF T-BUTYL TAXANE DERIVATIVES

(75) Inventor: Ramesh N. Patel, Bridgewater, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 611 days.

(21) Appl. No.: 10/223,800

(22) Filed: Aug. 20, 2002

(65) Prior Publication Data
US 2003/0069415 A1   Apr. 10, 2003

Related U.S. Application Data

(60) Provisional application No. 60/313,757, filed on Aug. 21, 2001.

(51) Int. Cl.
C12P 17/02 (2006.01)
C12P 17/10 (2006.01)
(52) U.S. Cl. ............. 435/280; 549/510; 549/511; 549/357; 435/123; 435/117; 435/197
(58) Field of Classification Search ............... None
See application file for complete search history.

(56) References Cited

U.S. PATENT DOCUMENTS

| 5,175,315 | A | 12/1992 | Holton |
| 5,227,400 | A | 7/1993 | Holton |
| 5,229,526 | A | 7/1993 | Holton |
| 5,243,045 | A | 9/1993 | Holton |
| 5,254,580 | A | 10/1993 | Chen |
| 5,274,124 | A | 12/1993 | Holton |
| 5,294,637 | A | 3/1994 | Chen |
| 5,336,785 | A | 8/1994 | Holton |
| 5,466,834 | A | 11/1995 | Holton |
| 5,808,102 | A | 9/1998 | Poss |
| 5,840,929 | A | 11/1998 | Chen |
| 6,750,246 | B1 | 6/2004 | Kadow et al. |
| 6,916,942 | B1 | 7/2005 | Kadow et al. |

FOREIGN PATENT DOCUMENTS

| EP | 0 590 267 A2 | 4/1994 |
| EP | 747385 | 12/1996 |
| WO | WO 94/14787 | 7/1994 |
| WO | WO 98/53811 | 12/1998 |

OTHER PUBLICATIONS

Seminars in Oncology 1999, 26 (1, Suppl 2).
Rowinsky et al. in TAXOL®: A Novel Investigational Antimicrotubule Agent, J. Natl. Cancer Instl, 82: pp. 1247-1259, 1990.
Rowinsky and Donehower in "The Clinical Pharamacology and Use of Antimicrotubule Agents in Cancer Chemotherapeutics," Pharmac. Ther., 52:35-84, 1991.
Spencer and Faulds in "Paclitaxel, A Review of its Pharmacodynamic and Pharmacokinetic Properties and Therapeutic Potential in the Treatment of Cancer," Drugs, 48 (5) 794-847, 1994.
K.C. Nicolaou et al. in "Chemistry and Biology of TAXOL®," Angew. Chem., Int. Ed. Engl., 33: 15-44, 1994.
F.A. Holmes, et al. "Taxane Anticancer Agents Basic Science and Current Status" edited by Gunda I. Georg, Thomas T. Chen, Iwao Ojima, and Dolotrai M. Vyas, 1995, American Chemical Society, Washington, DC, 31-57.
Susan G. Arbuck and Barbara Blaylock in the book "TAXOL® Science and Applications" edited by Mathew Suffness, 1995, CRC Press Inc., Boca Raton, Florida, 379-415.
Biologically Active Taxol Analogues with Deleted A-Ring Side Chain Substituents and Variable C-2' Configurations, J. Med. Chem., 34, pp. 1176-1184 (1991).
Structure of Taxol Analogues and Their Antimitotic, J. Med. Chem., 34, pp. 992-998 (1991).
Jorge E. Cortes and Richard Pazdur in Journal of Clinical Oncology 1995, 13(10), 2643 to 2655.
Eiseman et al., Second NCI Workshop on Taxol and Taxus (Sep. 1992).
J. Terwogt et al., from the Lancet, Jul. 25, 1998, vol. 352 p. 285.
U.S. Appl. No. 09/712,352.
Gunda I. Georg et al., Tetrahedron Letters, 1994, 35(48) 8931-8934.
S. Chen et al., in Journal of Organic Chemistry 1994, 59(21), 6156-8.
Chen, Shu-Hui. First synthesis of C-4 methyl ether paclitaxel analogs and the unexpected reactivity of 4-deacetyl-4-methyl ether baccatin III. Tetrahedron Lett. 1996, 37(23), 3935-3938.

(Continued)

Primary Examiner—Irene Marx
(74) Attorney, Agent, or Firm—Elliott Korsen

(57) ABSTRACT

A method for the resolution of a mixture of the cis or trans enantiomers of a compound of the formula

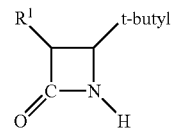

wherein $R^1$ is —O—C(O)alkyl, —O—C(O)aryl or —O—C(O)cycloalkyl by contacting the mixture with a carboxylic ester hydrolase enzyme which catalyzes the stereoselective hydrolysis of the mixture and the use of such enantiomers to produce antitumor compounds which are especially suitable for oral administration.

16 Claims, No Drawings

OTHER PUBLICATIONS

Chen, Shu-Hui; Wei, Jian-Mei; Long, Byron H.; Fairchild, Craig A.; Carboni, Joan; Mamber, Steven W.; Rose, William C.; Johnston, Kathy; Casazza, Anna M.; et al. Novel C-4 paclitaxel (Taxol) analogs: potent antitumor agents. Boorg. Med. Chem. Lett. 1995, 5(22), 2741-6.

Chen, Shu-Hui; Fairchild, Craig; Long, Byron H. Synthesis and Biological Evaluation of Novel C-4 Aziridine-Bearing Paclitaxel (Taxol) Analogs. J. Med. Chem. 1995, 38(12), 263-7.

Uoto, Kouichi; Takenoshita, Haruhiro; Ishiyama, Takashi; Terasawa, Hirofumi; Soga, Tsunehiko, Chem. Pharm. Bull. 1997, 45(12), 2093-2095.

Samaranayake, Gamini; Neidigh, Kurt A.; Kiingston, David G. I. Modified taxols, 8. Deacylation and reacylation of Baccatin III. J. Nat. Prod. 1993, 56(6), 884-98.

Datta, Apurba; Jayasinghe, Lalith R.; Georg, Gunda I.. 4-Deacetyltaxol and 10-Acetyl-4-deacetyltaxotere: Synthesis and Biological Evaluation. J. Med. Chem. 1994, 37(24), 4258-60.

Terwogt, Jetski M. Meerum; et al. Co-administration of oral cyclosporin A enables oral therapy with paclitaxel. Clin. Cancer Res. (1990), 5(11), 3379-3384.

Hansel, Steven B. A method of making taxanes orally bioavailable by coadministration with cinchonine. PCT Int. Appl. WO 97/27855 published Aug. 7, 1997.

Pratesi G. Polizzi D, Totoreto M, Riva A, Bombardelli E, Zunino F; IND5109 a new taxane active after oral administration. Proc Am Assoc Cancer Res 1999 40 Abs 1905, Istituto Nazionale Tumori, 20133 Milan and Indena SpA, 20139, Milan, Italy.

Nicoletti ML, Rossi C, Monardo C, Stura S, Morazzoni P, Bombardelli E, Valoti G, Giavazzi R.: Antitumor efficacy of the paclitaxel analogue, IDN5109, on human ovarian cacinoma xenografts with different sensitivity to the paclitaxel. Proc Am Assoc Cancer Res 1999 40 Abs 1910.

Polizzi, Donatella; Pratesi, Graziella; Tortoreto, Monica; Supino, Rosanna; Riva, Antonella; Bombardelli, Ezio; Zunino, Franco. A novel taxane with improved tolerability and therapeutic activity in a panel of human tumor xenografts. Cancer Res. 1999, 59(5), 1036-1040.

"Protective Groups in Organic Synthesis" by T. W. Greene, John Wiley and Sons, 1981, or Fiser & Fiser.

European Patent Application No. 400,971.

T.W. Greene in Chapter 2 of "Protecting Groups in Organic Synthesis", Third Ed., by Theodora W. Greene and Peter G. M. Wuts (1999, John Wiley & Sons, New York).

ENZYMATIC RESOLUTION OF T-BUTYL TAXANE DERIVATIVES

RELATED APPLICATION

This application claims benefit to provisional application U.S. Ser. No. 60/313,757, filed Aug. 21, 2001.

FIELD OF THE INVENTION

The present invention is directed to the enzymatic resolution of taxane derivatives and to methods of preparing orally active antitumor compounds from said taxane derivatives.

BACKGROUND OF THE INVENTION

Paclitaxel is a natural product extracted from the bark of Pacific yew trees, Taxus brevifolia and the active constituent of the anticancer agent TAXOL®. It has been shown to have excellent antitumor activity in in vivo animal models, and recent studies have elucidated its unique mode of action, which involves abnormal polymerization of tubulin and disruption of mitosis. It is used clinically against a number of human cancers. It is an important cancer agent both therapeutically and commercially. Numerous clinical trials are in progress to expand and increase the utility of this agent for the treatment of human proliferative diseases. The results of TAXOL® clinical studies have been reviewed by numerous authors. A very recent compilation of articles by a number of different authors is contained in the entire issue of Seminars on Oncology 1999, 26 (1, Suppl 2). Other examples are such as by Rowinsky et al. in TAXOL®: A Novel Investigational Antimicrotubule Agent, J. Natl. Cancer Instl, 82: pp 1247–1259, 1990; by Rowinsky and Donehower in "The Clinical Pharmacology and Use of Antimicrotubule Agents in Cancer Chemotherapeutics," Pharmac. Ther., 52:35–84, 1991; by Spencer and Faulds in "Paclitaxel, A Review of its Pharmacodynamic and Pharmacokinetic Properties and Therapeutic Potential in the Treatment of Cancer," Drugs, 48 (5) 794–847, 1994; by K. C. Nicolaou et al. in "Chemistry and Biology of TAXOL®," Angew. Chem., Int. Ed. Engl., 33: 15–44, 1994; by F. A. Holmes, A. P. Kudelka, J. J. Kavanaugh, M. H. Huber, J. A. Ajani, V. Valero in the book "Taxane Anticancer Agents Basic Science and Current Status" edited by Gunda I. Georg, Thomas T. Chen, Iwao Ojima, and Dolotrai M. Vyas, 1995, American Chemical Society, Washington, D.C., 31–57; by Susan G. Arbuck and Barbara Blaylock in the book "TAXOL® Science and Applications" edited by Mathew Suffness, 1995, CRC Press Inc., Boca Raton, Fla., 379–416; and also in the references cited therein.

A semi-synthetic analog of paclitaxel named docetaxel has also been found to have good antitumor activity and is the active ingredient of the commercially available cancer agent TAXOTERE®. See, Biologically Active Taxol Analogues with Deleted A-Ring Side Chain Substituents and Variable C-2' Configurations, J. Med. Chem., 34, pp 1176–1184 (1991); Relationships between the Structure of Taxol Analogues and Their Antimitotic Activity, J. Med. Chem., 34, pp 992–998 (1991) incorporated herein by reference. A review of the clinical activity of TAXOTERE® by Jorge E. Cortes and Richard Pazdur has appeared in Journal of Clinical Oncology 1995, 13(10), 2643 to 2655. The structures of paclitaxel and docetaxel are shown below along with the conventional numbering system for molecules belonging to the class; such numbering system is also employed in this application.

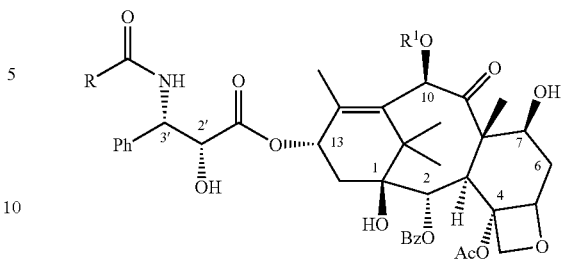

paclitaxel (TAXOL®): R=Ph; $R^1$=acetyl docetaxel (TAXOTERE®): R=t-butoxy; $R^1$=hydrogen Ample evidence that paclitaxel has no oral activity can be found within the following quote from PCT patent application WO 98/53811 by inventors Samuel Broder, Kenneth L. Duchin and Sami Selim and the references cited within the quote, which says: "Paclitaxel is very poorly absorbed when administered orally (less than 1%); see Eiseman et al., Second NCI Workshop on Taxol and Taxus (September 1992); Suffness et al., in TAXOL Science and Applications (CRC Press 1995). Eisemann et al., indicate that paclitaxel has a bioavailability of 0% upon oral administration and Suffness et al., report that oral dosing with paclitaxel did not seem possible since no evidence of antitumor activity was found on oral administration up to 160 mg/kg/day. Moreover, no effective method has been developed to enable the effective administration of oral paclitaxel (i.e., a method of increasing the oral bioavailability of paclitaxel) or of other oral taxanes or paclitaxel analogs such as docetaxel which exhibit antitumor activity. For this reason, paclitaxel has not until now been administered orally to human patients, and certainly not in the course or treating paclitaxel-responsive diseases." Another report by J. Terwogt et al., from the Lancet, Jul. 25, 1998, vol. 352 page 285 also describes the low bioavailability to doses as high as 160 mg/kg/inj in murine (mouse) tumor models (sc M109) without signs of any efficacy and have concluded, like Suffness, that further dosing would not provide efficacy even though toxic doses were not reached. Furthermore, our own attempts to demonstrate activity for orally administered paclitaxel against human tumor xenografts implanted in either athymic mice or athymic rates have to date been unsuccessful.

The present invention provides for the enzymatically resolution racemic mixtures of particular effective water soluble C-4 taxane analogs disclosed in copending U.S. patent application Ser. No. 09/712,352, incorporated herein by reference, which have oral activity and thus would have utility against proliferative diseases after oral administration. Some of the background art pertaining to this invention are shown below.

Certain taxane derivatives with modifications at the C-4 hydroxy group have been described in the art.

U.S. Pat. No. 5,808,102 to Poss et al., and PCT Published Patent Application No. WO 94/14787 contain descriptions of taxane analogs with modifications at the C-4 positions.

Gunda I. Georg et al., describe the synthesis of a C-4 ester analog in Tetrahedron Letters, 1994, 35(48) 8931–8934.

S. Chen et al., describe the synthesis of a C-4 cyclopropyl ester analog in Journal of Organic Chemistry 1994, 59(21), 6156–8.

U.S. Pat. No. 5,840,929 to Chen, Shu-Hui covering the C4 methoxy ether derivatives issued on Nov. 24, 1998.

Chen, Shu-Hui. First synthesis of C-4 methyl ether paclitaxel analogs and the unexpected reactivity of 4-deacetyl-4-methyl ether baccatin III. *Tetrahedron Lett.* 1996, 37(23), 3935–3938.

The following reference discusses a number of C-4 ester or carbonate analogs: Chen, Shu-Hui; Wei, Jian-Mei; Long, Byron H.; Fairchild, Craig A.; Carboni, Joan; Mamber, Steven W.; Rose, William C.; Johnston, Kathy; Casazza, Anna M.; et al. Novel C-4 paclitaxel (Taxol) analogs: potent antitumor agents. *Boorg. Med. Chem. Lett.* 1995, 5(22), 2741–6.

The preparation of C-4 aziridinyl carbamate analogs has been described in: Chen, Shu-Hui; Fairchild, Craig; Long, Byron H. Synthesis and Biological Evaluation of Novel C-4 Aziridine-Bearing Paclitaxel (Taxol) Analogs. *J. Med. Chem.* 1995, 38(12), 263–7.

The following papers describe reactions or transformations which are described as of C-4 analog preparation:

A new method to modify the C-4 position of 10-deacetylbaccatin III. Uoto, Kouichi; Takenoshita, Haruhiro; Ishiyama, Takashi; Terasawa, Hirofumi; Soga, Tsunehiko, *Chem. Pharm. Bull.* 1997, 45(12), 2093–2095.

Samaranayake, Gamini; Neidigh, Kurt A.; Kiingston, David G. I. Modified taxols, 8. Deacylation and reacylation of Baccatin III. *J. Nat. Prod.* 1193, 56(6), 884–98.

Datta, Apurba; Jayasinghe, Lalith R.; Georg, Gunda I. 4-Deacetyltaxol and 10-Acetyl-4-deacetyltaxotere: Synthesis and Biological Evaluation. *J. Med. Chem.* 1994, 37(24), 4258–60.

Inspite of the above-mentioned examples of C-4 analogs or methodology to prepare them, no evidence of orally active C-4 analogs has been supplied. The present invention provides a method of resolving racemic mixtures of C-4 analogs which have oral activity.

The following references describe methods or possible methods for orally active taxanes.

Methods for administering taxanes in the presence of modulators have been reported to increase the amount of taxanes in the plasma after oral administration: Terwogt, Jetske M. Meerum; Beijnen, Jos H.; Ten Bokkel Huinink, Wim W.; Rosing, Hilde; Schellens, Jan H. M. Coadministration of cyclosporin enables oral therapy with paclitaxel. Lancet (1998), 352 (9124), 285.

Terwogt, Jetski M. Meerum; Malingre, Mirte M.; Beijnen, Jos H.; Huinink, Wim W. ten Bokkel; Rosing, Hilde; Koopman, Franciska J.; Van Tellingen, Olaf; Swart, Martha; Schellens, Jan H. M. Co-administration of oral cyclosporin A enables oral therapy with paclitaxel. Clin. Cancer Res. (1990), 5(11), 3379–3384.

Hansel, Steven B. A method of making taxanes orally bioavailable by coadministration with cinchonine. PCT Int. Appl. WO 97/27855 published Aug. 7, 1997.

Broder, Samuel; Duchin, Kenneth L.; Selim, Sami. Method and compositions for administering taxanes orally to human patients using a cyclosporin to enhance bioavailability. PCT Int. Appl. WO 98/53811 published Dec. 3, 1998. These reports contain no antitumor efficacy data but the presence of taxanes in the plasma is extrapolated to show their potential for anticancer utility.

At least one report of oral activity of prodrugs in preclinical animal modes has appeared in the prior art: Scola, Paul M.; Kadow, John F.; Vyas, Dolatrai M. Preparation of paclitaxel prodrug derivatives. Eur. Pat. Appl. EP 747385 published Dec. 11, 1996. The oral bioavailability of the prodrug which had oral efficacy was not disclosed an no further reports of these compounds progressing to man have appeared.

Very recently, an abstract describing a taxane analog (IDN-5109) with oral activity against tumors in mice was disclosed at the American Association of Cancer Researchers in Philadelphia in 1999. The reference for the abstract is: Pratesi G. Polizzi D, Totoreto M, Riva A, Bombardelli E, Zunino F: IND5109 a new taxane active after oral administration. Proc Am Assoc Cancer Res 1999 40 Abs 1905, Istituto Nazionale Tumori, 20133 Milan and Indena SpA, 20139, Milan, Italy. The structure of this compound is quite different than compounds described in the present invention. Unlike the compounds encompassed by the present invention, IDN-1509 is derived from 14-betahydroxy baccatin III and has an acetate on the hydroxy group at the C-4 position.

Two references on the activity of this compound are included for completeness.

Nicoletti M L, Rossi C, Monardo C, Stura S, Morazzoni P, Bombardelli E, Valoti G, Giavazzi R.: Antitumor efficacy of the paclitaxel analogue, IDN5109, on human ovarian cacinoma xenografts with different sensitivity to the paclitaxel. *Proc Am Assoc Cancer Res* 1999 40 Abs 1910 [Evals+citations].

Polizzi, Donatella; Pratesi, Graziella; Tortoreto, Monica; Supino, Rosanna; Riva, Antonella; Bombardelli, Ezio; Zunino, Franco. A novel taxane with improved tolerability and therapeutic activity in a panel of human tumor xenografts. *Cancer Res.* 1999, 59(5), 1036–1040.

Paclitaxel is a highly schedule dependent drug that benefits traditionally from prolonged tumor exposure times. This relates to paclitaxel's mechanism of action as taxanes only recognize and bind to the polymerized state of tubulin which occurs only during a brief period of the cancer cell cycle. The currently used intravenous infusions (1–3 hours) are now readily accepted and efficacious and preclude the routine use of protracted (>24 hours) continuous schedules. However, an oral taxane may provide a compliant and cost effective way of accomplishing such extended duration of exposure. Recently, clinical utility has also been demonstrated using repetitive once weekly administrations of moderate (i.e., other than maximally tolerated) doses of TAXOL® and an oral taxane would be ideal for such protracted regimens. Other purported clinical indications for taxanes use (e.g., rheumatoid arthritis, multiple sclerosis) would also benefit from the availability of an oral taxane. An orally administered effective taxane would offer both an attractive alternative from the parenteral from the format of current clinical taxane usage, and a potential therapeutic advantage because of the many avenues of scheduling yet to be investigated.

Thus, it is clear there is a great need to provide taxanes in a pure, highly resolved form with both good oral bioavailability and good oral efficacy, which are comparable to paclitaxel administered parenterally.

SUMMARY OF THE INVENTION

The present invention provides, in part, efficient methods for the resolution of enantiomeric mixtures, preferably racemic mixtures, of compounds identified as particularly useful as intermediates in the preparation of orally administered taxanes such as taxol, and thus for the stereospecific preparation of these compounds. In a further aspect of the invention the resolved enantiomers are used to prepare taxanes useful for oral administration to warm blooded animals including humans.

Specifically, the present invention provides a method for the resolution of a mixture comprising the enantiomers of formulas Ia and Ib, where $R^1$ is in the cis position relative to the t-butyl group in both formulas Ia and Ib as shown below.

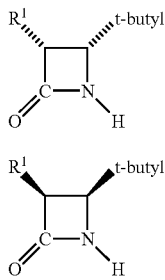

Ia

Ib or where $R^1$ is in the trans position relative to t-butyl group in both formulas IIa and IIb:

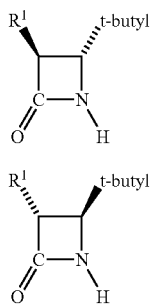

IIa

IIb where $R^1$ is —O—C(O)alkyl, —O—C(O) aryl or —O—C(O) cycloalkyl;

comprising the steps of (a) contacting said mixture with a carboxylic ester hydrolase enzyme or a microorganism providing a carboxylic ester hydrolase enzyme, wherein said enzyme catalyzes the stereoselective hydrolysis of said mixture to provide a mixture of two compounds in which in one compound $R^1$ is —O—C(O)alkyl, —O—C(O)aryl or —O—C(O)cycloalkyl and in the other compound $R^1$ is hydroxy, and (b) recovering one or both of said compounds.

DETAILED DESCRIPTION OF THE INVENTION

The methods of the present invention are described further as follows.

Cis Enantiomers

The following pair of cis enantiomers may be separated by the enzymatic methods of the instant invention:

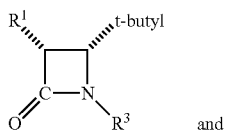

Ia and

-continued

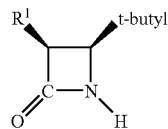

Ib that is, enantiomers of formulas Ia and Ib where $R^1$ is in the cis position relative to the t-butyl group in both Ia and Ib.

It is preferred to resolve a mixture of cis enantiomers as described above according to the methods of the instant invention.

Trans Enantiomers

The following pair of trans enantiomers may be separated by the enzymatic methods of the instant invention:

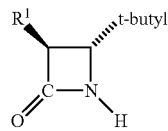

IIa and

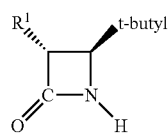

IIb that is, enantiomers of formulas IIa and IIb where $R^1$ is in the trans position relative to the t-butyl group in both.

Preferred Methods for the Resolution of Mixtures of Enantiomers

A mixture comprising an enantiomeric mixture of compounds of formulas Ia and Ib or IIa and IIb are preferably resolved by stereoselective hydrolysis in the presence a carboxylic ester hydrolase enzyme, preferably from a microorganism.

The compound pairs so prepared are non-enantiomeric and may subsequently be separated to yield optically active, preferably optically pure, compounds. An optical purity greater than 99%, particularly 99.5%, is preferred.

The present invention also provides a compound of the mixture substantially free of other isomers, which compounds may be prepared by the methods of the invention.

In addition, the present invention is directed to a process of preparing select taxane compounds using intermediate compounds obtained by the methods described above.

Definitions

The term "stereoselective conversion", as used herein, refers to the preferential reaction of one enantiomer relative to another, that is, asymmetric, enantioselective, reaction. Likewise, the term "stereoselective hydrolysis", refers to the preferential hydrolysis, of one enantiomer relative to another.

The term "mixture", as said term is used herein in relation to enantiomeric compounds, denotes mixtures having equal (racemic) or non-equal amounts of enantiomers.

The term "resolution" as used herein denotes partial, as well as, preferably, complete resolution.

The term "non-enantiomeric form" as used herein denotes the structure of a compound, originally one of an enantiomeric pair, in which at least one group has been modified so that said compound is no longer the mirror image of the other compound of the original enantiomeric pair.

The terms "enzymatic process" or "enzymatic method" as used herein denote a process or method of the present invention employing an enzyme or microorganism.

The terms "alkyl", "alkan" or "alk" are employed herein alone or as part of another group preferably denote both straight and branched chain, optionally substituted hydrocarbons containing 1 to 15 carbons in the normal chain, preferably 1 to 6 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. Exemplary substituents may include one or more groups selected from the following: halo (especially chloro), trihalomethyl, alkoxy (for example, where two alkoxy substituents form an acetal), aryl such as unsubstituted aryl, alkyl-aryl or haloaryl, cycloalkyl such as unsubstituted cycloalkyl or alkyl-cycloalkyl, hydroxy or protected hydroxy group, carboxyl, alkyloxycarbonyl, alkylamino, alkylcarbonylamino, amino arylcarbonylamino, nitro, cyano, thiol or alkylthio. Particularly preferred alkyl substitutents are hydroxyl groups.

The term "cycloalkyl" as employed herein alone or as part of another group preferably denotes optionally substituted saturated cyclic hydrocarbon groups containing one to three rings and 3 to 12 ring carbons, preferably 3 to 8 ring carbons, which include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The term "aryl" as employed herein preferably denotes monocyclic or bicyclic substituted aromatic groups containing from 6 to 12 carbon atoms in the ring portion such as unsubstituted phenyl, biphenyl, naphthyl, or substituted with substituents such as alkyl, haloalkyl, cycloalkylalkyl, halogen, alkoxy, haloalkoxy, hydroxy, aryl and the like.

The term "hydroxyl protecting group" as used herein denotes a group capable of protecting a free hydroxyl group which, subsequent to the reaction for which protection is employed, may be removed without disturbing the remainder of the molecule. A variety of protecting groups for the hydroxyl group and the synthesis thereof may be found, for example, in "Protective Groups in Organic Synthesis" by T. W. Greene, John Wiley and Sons, 1981, or Fiser & Fiser incorporated herein by reference. Exemplary hydroxyl protecting groups include methoxymethyl, 1-ethoxyethyl, benzyloxymethyl, (β-trimethylsilylethoxy) methyl, tetrahydropyranyl, 2,2,2-trichloroethoxy-carbonyl, t-butyl(diphenyl) silyl, trialkylsilyl, trichloromethoxycarbonyl and 2,2,2-trichloroethoxymethyl.

Starting Materials

A mixture of starting materials comprising compounds of formulas Ia and Ib may be prepared by methods known to the skilled artisan, such as those described in European Patent Application No. 400,971, incorporated herein by reference. For example, a racemic mixture of cis-β-lactam compounds of formulas Ia and Ib may be prepared by the formation of an imine of the formula:

by reaction of an aldehyde of the formula:

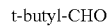

The imine so prepared may then be reacted with an acyl chloride of the formula:

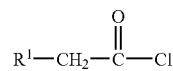

Wherein $R^1$ is as defined previously, such as acetoxy acetyl chloride, to produce a racemic mixture of cis-β-lactam compounds of the formulas Ia and Ib. The latter reaction may be conducted in the presence of a base such as triethylamine in a solvent such as methylene chloride at a temperature such as −20° C., followed by warming to 25° C.

The above procedure may, in turn, be followed by modification of the lactam formed, should a different lactam starting material be desired.

Starting mixtures which are other than racemic mixtures may be obtained, for example, by addition of one of the compounds formulas Ia or Ib to a racemic mixture of the compounds.

The starting mixture may contain, for example, the diastereomers of the compounds of formulas Ia and Ib, although it is preferred that such compounds are separated prior to conducting the enzymatic resolution methods of the present invention.

Enzymes and Microorganisms

The enzyme or microorganism employed in the methods of the present invention may be any enzyme or microorganism having the ability to catalyze the stereoselective conversions as described herein. Various enzymes, such as esterases, lipases amidases and acylases, regardless of origin or purity may, for example, be in the form of animal or plant enzymes or mixtures thereof, cells of microorganisms, crushed cells, extracts of cells, or of synthetic origin.

With respect to the use of microorganisms, the methods of the present invention may be carried out using any microbial cellular material having the ability to catalyze the stereoselective conversions as described herein. The cells may be used in the form of intact wet cells or dried cells such lyophilized, spray-dried or heat-dried cells. Cells may also be used in the form of treated cell material such as ruptured cells or cell extract. The cells or cellular materials may be cells or cell extract. The cells or cellular materials may be employed in the free state or immobilized on a support such as by physical adsorption or entrapment.

Exemplary genera of microorganisms suitable as sources of catalyzing enzymes include *Mucor, Escherichia, Staphylococcus, Agrobacterium, Acinetobacter, Rhizopus, Aspergillus, Nocardia, Streptomyces, Trichoderma, Candida, Rhodotorula, Torulopsis, Proteus, Bacillus, Alcaligenes, Psuedomonas, Rhodococcus, Brevibacterium, Geotrichum, Enterobacter, Chromobacterium, Arthrobacter, Microbacterium, Mycobacterium, Saccharomyces, Penicillium, Methanobacterium, Botrytis, Chaetomium, Ophiobolus, Cladosporium* and the like. The use of genetically engineered host cells is also contemplated.

Specific microorganisms suitable for use in the present processes include *Chromobacterium viscosum, Pseudomonas aeuriginosa* such as ATCC 25619, *Pseudomonas fluorescens, Pseudomonas putida* such as ATCC 31303, *Pseudomonas ovalis, Escherichia coli, Staphylococcus aureas, Alcaligenes faecalis, Streptomyces griseus,*

Pseudomonas cepacia, Candida rugosa such as ATCC 14830, Geotrichum candidum such as ATCC 32345, Streptomyces clavuligerus, Nocardia erythropolis, Nocardia asteraides, Mycobacterium phlei, Agrobacterium radiobacter, Aspergillus niger, Rhizopus oryzae and the like. Two or more, as well as a single, species of microorganism may be employed when carrying out the instant processes. The term "ATCC" as used herein refers to the accession number of the American Type Culture Collection, 12301 Parklawn Drive, Rockville, Md. 20852, the depository for the organism referred to.

The resolution methods of the instant invention may be carried out subsequent to the growth of the microorganism(s) employed, or concurrently therewith that is, in the latter case, by in situ fermentation and resolution. The growth of microorganisms may be achieved by the skilled artisan, for example, by the use of an appropriate medium containing nutrients such as carbon and nitrogen sources and trace elements.

Exemplary, commercially available enzymes suitable for use in the present invention include lipases such as Amano PS-30 (*Pseudomonas cepacia*), Amano GC-20 (*Geotrichum candidum*), Amano APF (*Aspergillus niger*), Amano AK (*Pseudomonas* sp.), *Pseudomonas fluorescens* lipase (Biocatalyst Ltd.), Amano Lipase P-30 (*Pseudomonas* sp.), Amano P (*Pseudomonas fluorescens*), Amano AY-30 (*Candida cylindracea*), Amano N (*Rhizopus niveus*), Amano R (*Penicillium* sp.), Amano FAP (*Rhizopus oryzae*), Amano AP-12 (*Aspergillus niger*), Amano MAP (*Mucor meihei*), Amano GC-4 (*Geotrichum candidum*), Sigma L-0382 and L-3126 (porcine pancrease), Sigma L-3001 (Wheat germ), Sigma L-1754 (*Candida cylindracea*), Sigma L-0763 (*Chromobacterium viscosum*) and Amano K-30 (*Aspergillus niger*). Additionally, exemplary enzymes derived from animal tissue include esterase from pig liver, α-chymotrypsin and pancreatin from pancreas such as Porcine Pancratic Lipase (Sigma). Two or more, as well as a single, enzyme may be employed when carrying out the instant processes.

The preferred embodiments of the instant invention are described further in the following Reaction Schemes. While, for clarity, these Reaction Schemes illustrate the resolution of certain cis enantiomeric mixtures, it is understood that the embodiments as described apply to the resolution of the other enantiomeric mixtures of the present invention as well.

EXAMPLE 1

Resolution of Racemic
cis-3-4-t-butyl-3-acetyloxyazitidin-2-one by
Immobilized Lipase PS-30 from *Pseudomonas cepacia*

A reaction mixture was prepared containing 3 liters of 10 mM potassium phosphate buffer, 90 g of racemic cis-3-4-t-butyl-3-acetyloxyazitidin-2-one and 45 g of immobilized lipase PS-30 *Pseudomonas cepacia*. The reaction was carried out at 40° C. under stirring at 150 rpm. The pH of the reaction mixture was maintained at 7.0 with a 25% NaOH solution. After 4 hours the reaction yielded 49% of the desired chiral acetate (thereotical maximum yield of 50%) and a enantiomeric excess purity of greater than 99%.

EXAMPLE 2

Resolution of Racemic
cis-3-4-t-butyl-3-acetyloxyazitidin-2-one by Pen V
amidase Immobilized from *Fusarium* Sp A reaction mixture was prepared containing 20 ml of 10 mM potassium phosphate buffer, 100 mg of racemic cis-3-4-t-butyl-3-acetyloxyazitidin-2-one and 25 mg of immobilized Pen V amidase from *Fusarium* Sp. The reaction was carried out at 40° C. under stirring at 150 rpm. The pH of the reaction mixture was maintained at 7.0 with a 0.1N NaOH solution. After 3 hours the reaction yielded 36% of the desired chiral acetate (thereotical maximum yield of 50%) and a enantiomeric excess of greater than 90%.

EXAMPLE 3

Resolution of Racemic
cis-3-4-t-butyl-3-propionyloxyazitidin-2-one by
Immobilized Lipase PS-30 from *Pseudomonas cepacia* and Pen V amidase from *Fusarium* Sp A reaction mixture was prepared containing 20 ml of 10 mM potassium phosphate buffer, 100 mg of racemic cis-3-4-t-butyl-3-propionyloxyazitidin-2-one and 50 mg of immobilized lipase PS-30 from *Pseudomonas cepacia*. The reaction was carried out at 40° C. under stirring at 150 rpm. The pH of the reaction mixture was maintained at 7.0 with a 0.1N NaOH. After 18 hours the reaction yielded 48% of the desired chiral propionate (thereotical maximum of 50%) and a enanliomeric excess of greater than 99%.

A reaction mixture was prepared containing 20 ml of 10 mM potassium phosphate buffer, 100 mg of racemic cis-3-4-t-butyl-3-propionyloxyazitidin-2-one and 25 mg of immobilized Pen V amidase from *Fusarium* Sp. The reaction was carried out at 40° C. under stirring at 150 rpm. The pH of the reaction mixture was maintained at 7.0 with a 0.1N NaOH. After 20 minutes the reaction yielded 25% of the desired chiral propronate (thereotical maximum of 50%) and a enantiomeric excess of greater than 98%.

EXAMPLE 4

Resolution of Racemic
cis-3-4-t-butyl-3-hexanoyloxyazitidin-2-one by
Immobilized Lipase PS-30 from *Pseudomonas cepacia*

A reaction mixture was prepared containing 20 ml of 10 mM potassium phosphate buffer, 100 mg of racemic cis-3-4-t-butyl-3-hexanoyloxyazitidin-2-one and 50 mg of immobilized lipase PS-30 from *Pseudomonas cepacia*. The reaction was carried out at 40° C. under stirring at 150 rpm. The pH of the reaction mixture was maintained at 7.0 with a 0.1N NaOH. After 30 minutes the reaction yielded 48% of the desired chiral hexanoyl (thereotical maximum of 50%) and a enantiomeric excess of greater than 99%.

EXAMPLE 5

Resolution of Racemic
cis-3-4-t-butyl-3-phenylacetyloxyazitidin-2-one by
Pen V amidase from *Fusarium* Sp A reaction mixture was prepared containing 20 ml of 10 mM potassium phosphate buffer, 100 mg of racemic cis-3-

4-t-butyl-3-phenylacetyloxyazitidin-2-one and 25 mg of immobilized Pen V amidase from *Fusarium* Sp. The reaction was carried out at 40° C. under stirring at 150 rpm. The pH of the reaction mixture was maintained at 7.0 with a 0.1N NaOH. After 18 hours the reaction yielded 25% of the desired chiral phenylacetyl (thereotical maximum of 50%) and a enantiomeric excess of greater than 99%.

The optically active enantiomers disclosed herein can be employed to produce antitumor compounds represented by formula III, or pharmaceutically acceptable salts thereof.

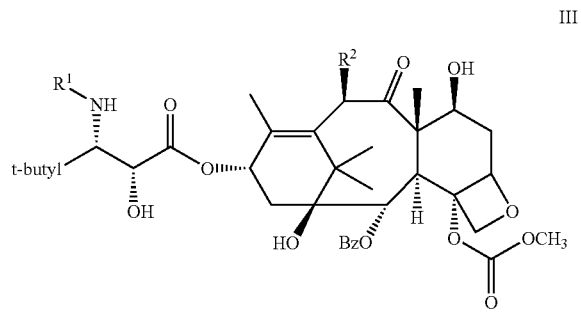

III wherein:
$R^1$ is as defined above; and
$R^2$ is $CH_3C(O)O$—.

A particularly preferred compound is where $R^1$ is O—C(O)-tert butyl.

The compounds having the general formula III display a significant inhibitory effect with regard to abnormal cell proliferation, and have therapeutic properties that make it possible to treat patients who have pathological conditions associated with an abnormal cell proliferation. In addition, these compounds possess significant oral bioavailability and thus can elicit their positive therapeutic effects after being administered orally.

A compound of formula III may be produced by the processes as depicted in Scheme 1 which follow. The methods can be readily adapted to variations in order to produce compounds within the scope of formula III but not specifically disclosed.

One of the ways the desired compounds can be made is by the general method shown in Scheme 1. In step (a) of the scheme, an entanomer of formulas Ia, Ib, IIa, or IIb as previously described above is reacted with a compound of formula IV (a baccatin III derivative).

In Step (a) of Scheme 1, it is advantageous to convert the hydroxy group on the (C) 13-carbon into a metal alkoxide before the coupling. The formulation of a desired metal alkoxide may be done by reacting a compound of formula IV with a strong metal base, such as lithium diisopropylamide, C1–6 alkyllithium, lithium or sodium or potassium bis(trimethylsilyl)amide, phenyllithium, sodium hydride, potassium hydride, lithium hydride, or the like base. For example when lithium alkoxide is desired, a compound of formula IV may be reacted with n-butyllithium in an inert solvent such as tetrahydrofuran. For examples of attachment of substituted baccatins with a suitable compound of formulas Ia, Ib, IIa or IIb via the method of Holton see U.S. Pat. No. 5,175,315; U.S. Pat. No. 5,466,834; U.S. Pat. No. 5,229,526; U.S. Pat. No. 5,274,124; U.S. Pat. No. 5,243,045; U.S. Pat. No. 5,227,400; U.S. Pat. No. 5,336,785; and U.S. Pat. No. 5,254,580; U.S. Pat. No. 5,294,637; or EP 0 590 267 A2, each of which is incorporated herein by reference.

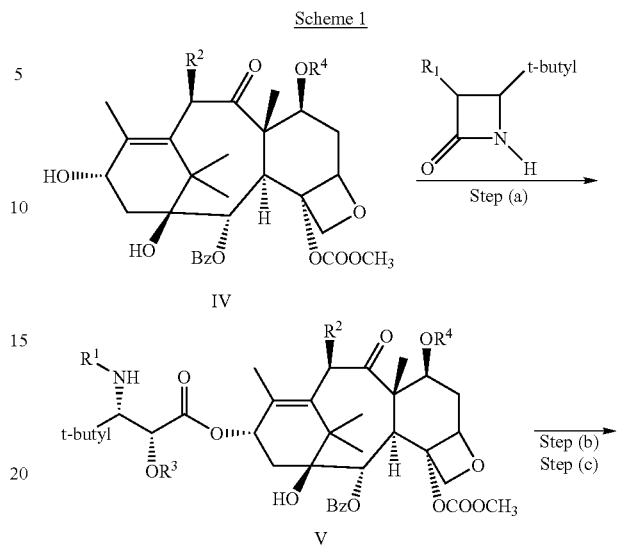

Scheme 1

As used herein, $R^3$ and $R^4$ are conventional hydroxy protecting groups as shown in formula V and as discussed previously. Conventional hydroxy protecting groups are moieties which can be employed to block or protect a hydroxy function, and they are well known to those skilled in the art. Preferably, said groups are those which can be removed by methods which result in no appreciable destruction to the remaining portion of the molecule. Examples of such readily removable hydroxy protecting groups include chloroacetyl, methoxymethyl, 1-methyl-1-methoxyethyl, tetrahydropyranyl, tetrahydrothiopyranyl, dialkysilylethers, such as dimethylsilyl ether, and trialkysilyl ethers such as trimethylsilyl ether, triethylsilyl ether, and t-butyldimethylsilyl ether, dialkyl alkoxy silyl ethers such as diisopropyl methoxy silyl ethers; 2,2,2-trichloroethyoxymethyl, 2,2,2-trichloroethyloxycarbonyl (or simply trichloroethyloxycarbonyl), benyloxycarbonyl and the like. Other suitable hydroxy protecting groups which may be used may be found in T. W. Greene discussed previously, as well as in Chapter 2 of "Protecting Groups in Organic Synthesis", Third Ed., by Theodora W. Greene and Peter G. M. Wuts (1999, John Wiley & Sons, New York), incorporated herein by reference. A protecting group for formula IV compounds which has been used frequently in the literature is trialkylsilyl. The most preferred groups for $R^3$ include 1-methyl-1-methoxyethyl (MOP), a trialkyl silyl ether, or a dialykyl silyl ether such as diisopropylmethoxy silyl ether.

The most preferred group for $R^4$ is a dialkyl alkoxy silyl ether such as a diisopropyl methoxy silyl ether but a trialkyl silyl ether or a carbonate such as a benzyl carbonate might also be preferred. In Step (b), the protecting group $R^3$ or $R^4$ or possibly both are removed from the compounds of formula V. If $R^3$ or $R^4$ is a silyl based protecting group, removal is effected by triethylamine trihydrofluoride in THF solvent. Other fluoride sources could also be utilized. For example tetrabutyl ammonium fluoride, pyridinium hydrofluoride, potassium fluoride, or cesium fluoride may find utility. The potassium fluoride may be utilized in combination with a complexing agent such as 18-crown-6 or the like to aid in desilylation. A solvent such as acetonitrile is typically used under these conditions. Other conditions such as mild aqueous hydrochloride acid or trifluoroacetic acid and a cosolvent such as acetonitrile or THF may be useful for deprotection of the silyl groups. The same acidic conditions work well to remove the 1-methyl-1-methoxyethyl (MOP) protecting group.

The conditions actually employed will depend on the protecting groups employed for $R^3$ or $R^4$. For example one preferred route might employ a MOP group for $R^3$ and a diisopropyl methoxy silyl ether for $R^4$. In this case, step (b) would entail a mild acidic workup using aqueous hydrochloric acid and an organic solvent. The resulting 2' deprotected compound would be exposed to a fluoride source such as triethylamine trihydorfluoride in THF solvent in step (c) to produce compound III after chromatographic or crystallographic purification.

What is claimed is:

1. A method for the resolution of a mixture comprising the enantiomers of formulas Ia and Ib, wherein $R^1$ is the cis position relative to t-butyl group in both formulas Ia and Ib:

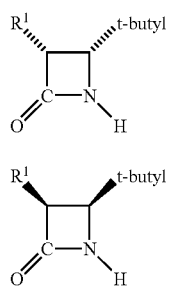

or where $R^1$ is in the trans position relative to t-butyl group in both formulas IIa and IIb:

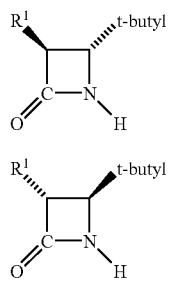

where
$R^1$ is —O—C(O) alkyl, —O—C(O) aryl or —O—C(O) cycloalkyl;
comprising the steps of (a) contacting said mixture with a carboxylic ester hydrolase enzyme which is a microbial amidase, or a microorganism which produces the amidase, wherein said enzyme catalyzes the stereoselective hydrolysis of said mixture to provide a mixture of two compounds in which in one compound $R^1$ is —O—C(O) alkyl, —O—C(O)-aryl or —O—C(O) cycloalkyl and in the other compound $R^1$ is hydroxy, and (b) recovering one or both of said compounds.

2. The method of claim 1, wherein said mixture is resolved in the presence of water and/or an organic alcohol.

3. The method of claim 2, wherein $R^1$ is —O—C(O)-alkyl.

4. The method of claim 3, wherein the compounds formed in step (a) have the following structures:

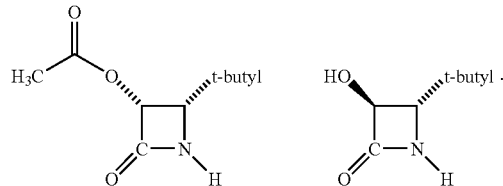

5. The method of claim 3, wherein the compounds formed in step (a) have the following structures:

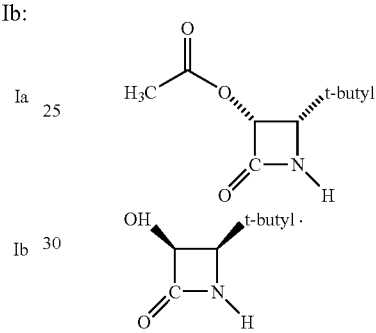

6. The method of claim 1, wherein the enzyme is immobilized on a support.

7. The method of claim 1 wherein the enzyme is Pen V amidase obtained from *Fusarium* sp.

8. A method of preparing a compound of formula III

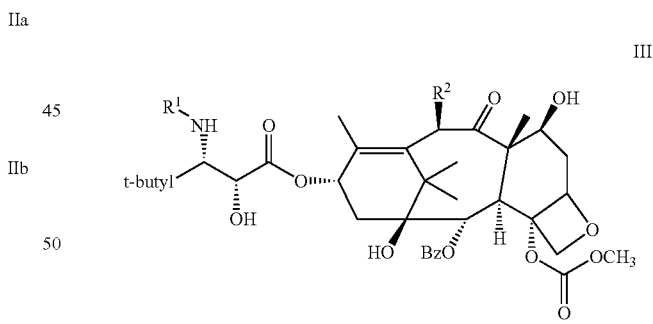

wherein:
BzO is

or benzoyl:
$R^1$ is —O—C(O) alkyl, —O—C(O) aryl or —O—C(O) cycloalkyl; and
$R^2$ is $CH_3C(O)O$—, comprising reacting an enantiomer selected from formulas Ia or Ib, or IIa or and IIb

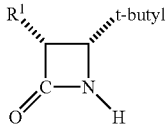
Ia

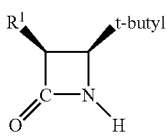
Ib

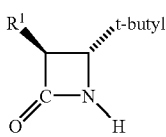
IIa

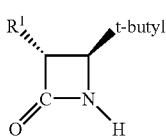
IIb wherein the enantiomers Ia and Ib are resolved from a mixture thereof and enantionmers IIa and IIb are resolved from a mixture thereof, each by the method as defined in claim 1 where $R^1$ is —O—C(O) alkyl, —O—C(O)-aryl or O—C(O) cycloalkyl; with a compound of formula IV

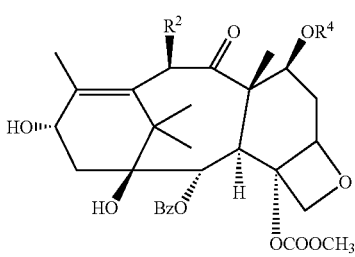
IV where

BzO is benzoyl;

wherein $R^2$ is $CH_3C(O)O$—;

and $R^4$ is a protecting group and removing the $R^4$ group to form a compound of formula III.

9. The method of claim 8 further comprising reacting the compound of formula IV with a strong metal base to convert the C-13 hydroxy group into a metal alkoxide.

10. A method for the resolution of a mixture comprising the enantiomers of formulas Ia and Ib, wherein $R_1$ is the cis position relative to the t-butyl group in both formulas Ia and Ib:

Ia

Ib where $R^1$ is —O—C(O) alkyl, —O—C(O) aryl or —O—C(O) cycloalkyl;

comprising the steps of (a) contacting said mixture with a carboxylic ester hydrolase enzyme which is a microbial amidase or a microorganism which produces the amidase, wherein said enzyme catalyzes the stereoselective hydrolysis of said mixture to provide a mixture of two compounds in which in one compound $R^1$ is —O—C(O) alkyl, —O—C(O)-aryl or —O—C(O) cycloalkyl and in the other compound $R^1$ is hydroxy, and (b) recovering one or both of said compounds.

11. The method of claim 10, wherein $R^1$ is —O—C(O)-alkyl.

12. The method of claim 11, wherein the compounds formed in step (a) have the following structures:

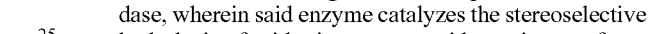

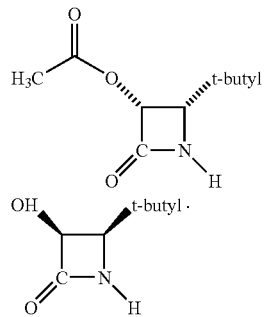

13. The method of claim 10 wherein the enzyme is immobilized on a support.

14. The method of claim 10 wherein the enzyme is Pen V amidase obtained from *Fusarium* sp.

15. A method of preparing a compound of formula III

III

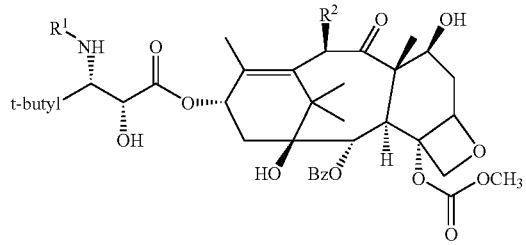

wherein:
   BzO is benzoyl;
   $R^1$ is —O—C(O) alkyl, —O—C(O) aryl or —O—C(O) cycloalkyl; and
   $R^2$ is $CH_3C(O)O$—,
   comprising reacting a compound selected from enantiomers formulas Ia or Ib

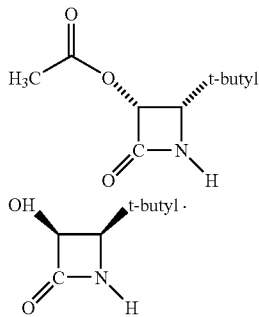

wherein the enantiomers Ia and Ib are resolved from a mixture thereof by the method as defined in claim 10, where
   $R^1$ is —O—C(O) alkyl, —O—C(O)-aryl or —O—C(O) cycloalkyl;

with a compound of formula IV

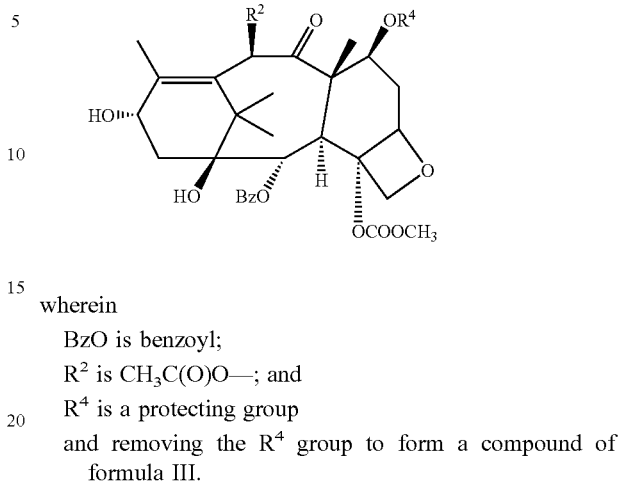

wherein
   BzO is benzoyl;
   $R^2$ is $CH_3C(O)O$—; and
   $R^4$ is a protecting group
   and removing the $R^4$ group to form a compound of formula III.

16. The method of claim 15 further comprising reacting the compound of formula IV with a strong metal base to convert the C-13 hydroxy group into a metal alkoxide.

* * * * *